(12) United States Patent
Fredenburgh

(10) Patent No.: US 7,329,533 B2
(45) Date of Patent: Feb. 12, 2008

(54) UNIT FOR THE TREATMENT OF HISTOLOGICAL SAMPLES

(75) Inventor: Jerry Fredenburgh, Plainwell, MI (US)

(73) Assignee: Microm International GmbH, Walldorf (DE)

(*) Notice: Subject to any disclaimer, the term of this patent is extended or adjusted under 35 U.S.C. 154(b) by 797 days.

(21) Appl. No.: 10/495,966

(22) PCT Filed: Dec. 11, 2002

(86) PCT No.: PCT/EP02/14036

§ 371 (c)(1),
(2), (4) Date: May 19, 2004

(87) PCT Pub. No.: WO03/054519

PCT Pub. Date: Jul. 3, 2003

(65) Prior Publication Data

US 2005/0002830 A1    Jan. 6, 2005

(30) Foreign Application Priority Data

Dec. 21, 2001   (DE) .............................. 101 63 488

(51) Int. Cl.
G01N 1/00 (2006.01)
G01N 1/10 (2006.01)
C12M 1/36 (2006.01)
C12M 3/00 (2006.01)

(52) U.S. Cl. ............... 435/286.5; 436/174; 436/176; 436/180; 435/301

(58) Field of Classification Search ............... 435/286.5
See application file for complete search history.

(56) References Cited

U.S. PATENT DOCUMENTS

| | | | | | |
|---|---|---|---|---|---|
| 5,073,504 A | * | 12/1991 | Bogen | ...................... | 436/174 |
| 5,273,905 A | * | 12/1993 | Muller et al. | ............ | 435/286.5 |
| 5,312,758 A | * | 5/1994 | Ahlqvist | ...................... | 436/63 |
| 5,560,956 A | | 10/1996 | Schmehl | | |
| 5,686,313 A | * | 11/1997 | Sitte et al. | ................... | 436/176 |
| 5,965,454 A | * | 10/1999 | Farmilo et al. | ............. | 436/180 |
| 6,080,365 A | * | 6/2000 | Thiem et al. | ................. | 422/99 |

FOREIGN PATENT DOCUMENTS

| | | |
|---|---|---|
| DE | 37 20 543 | 1/1988 |
| DE | 36 34 976 | 9/1997 |
| DE | 196 52 339 | 6/1998 |
| DE | 199 45 621 | 4/2001 |
| EP | 0 969 277 | 1/2000 |

* cited by examiner

*Primary Examiner*—Walter D. Griffin
*Assistant Examiner*—Lydia Edwards
(74) *Attorney, Agent, or Firm*—Paul Vincent

(57) ABSTRACT

The invention relates to a unit for the treatment of histological samples. The unit comprises a treatment chamber (1), a device (2) for supplying and removing treatment agents (3, 3', 3") to and from the treatment chamber (1), and a control system (4) for the performance of the treatment. The aim of the invention is to develop the unit in such a way that the need to carry out different treatments is taken into account in an economical manner. Towards this end, at least one other treatment chamber (5) is provided, by means of which treatments can be carried out independently from the first treatment chamber (1), the device (2) and the control system (4) also co-operating with that other treatment chamber (5).

16 Claims, 3 Drawing Sheets

UNIT FOR THE TREATMENT OF HISTOLOGICAL SAMPLES

This application is the national stage of PCT/EP02/14036 filed on Dec. 11, 2002 and claims Paris Convention priority of DE 101 63 488.9 filed Dec. 21, 2001.

BACKGROUND OF THE INVENTION

The invention concerns a device for the treatment of histological samples, comprising a treatment chamber and a means for supplying and removing treatment agents to and from the treatment chamber and with a controller for carrying out the treatment, including supplying and removing the required treatment agents.

A device of this type is disclosed e.g. in EP 0 969 277 A1. Such devices are used to prepare histological samples for microscopic examinations, wherein the samples removed for examination are subjected to a series of successive processing steps, such as fixation, e.g. in an aqueous formaldehyde solution, dehydration, clearing and infiltration with paraffin or another suitable wax. During dehydration, the fixed samples are treated with an alcohol reagent of gradually increasing concentration. During clearing, the dehydrated samples are treated once or several times with a clearing agent, e.g. xylol. The latter is an intermediate agent which facilitates removal of alcohol and subsequent introduction of paraffin, since direct replacement of alcohol by paraffin is not possible. Clearing also increases the contrast. For infiltration with paraffin (or another wax), the dehydrated and cleared samples are also immersed several times into molten wax. Only thereafter is the histological sample suited for processing with a microtome. Thin slices are thereby produced for examination under a microscope.

The above-mentioned conventional devices have one single treatment chamber which is divided into several chambers for receiving samples (EP 0 969 277 A1). The samples can only be filled into this single treatment chamber and can only be treated together. This procedure is normally followed by a program run in which the daily production is further processed overnight.

These methods fail to satisfy all requirements, in particular in the medical field, since different treatments must often be carried out or smaller amounts must be processed as rapidly as possible. Even if the above-mentioned device is designed for expedited treatment, usually only a small amount of samples must nevertheless be treated. This is normally the case with biopsy samples, which are suitable for rapid processing due to their considerably smaller size compared to that of other samples. Such small amounts do not usually fill the large treatment chamber, causing uneconomical processing. To avoid bottlenecks, i.e. when different treatments must be carried out or to avoid the above-mentioned uneconomical handling, several devices could be provided for different treatments, optionally having different program steps and different treatment chamber sizes. However, this would also be uneconomical, since several controllers and treatment agent supplying and removing units must be provided, maintained and filled. Moreover, many laboratories do not have the space required for several devices.

It is therefore the underlying purpose of the present invention to further develop a device of the above-mentioned type such that different treatments are possible with little economic expense.

This object is achieved in accordance with the invention in that at least one further treatment chamber is provided for carrying out treatment independently of the first treatment chamber, wherein the means and the controller also cooperate with the second treatment chamber.

The invention meets the requirement of economical treatment of small amounts of samples and/or different treatments of smaller or larger sample amounts using one single device, one controller and one means for supplying and removing treatment agents. The treatments may be carried out simultaneously or staggered in time. In the latter case, samples can be advantageously supplied to a treatment chamber while another or several other treatments are still running. The size of the treatment chambers can be adjusted to the amount and size of the sample charges to be expected, which advantageously saves treatment agent. The treatment chambers can also be adjusted to the samples to be processed or to different sample holders or can be optimised to certain types of treatment. All this can be realized with one device, one controller, one treatment agent supply, and optionally treatment agent stock which saves costs, space and effort with regard to maintenance and supply.

The following further developments of the invention contribute to the versatility of use of the inventive device and to its efficiency.

SUMMARY OF THE INVENTION

The treatment chambers are preferably designed for different procedures. It is e.g. often the case that short programs are used for processing small amounts of urgent samples. For this reason, the treatment chambers should have different sizes. The main treatment chamber may have a normal size and a further treatment chamber may be substantially smaller than that first treatment chamber.

The treatment chambers may also have different equipment which can be adapted to the different treatments or to different supports on which the samples are disposed. One further treatment chamber may be designed to receive biopsy samples.

The controller is preferably designed to carry out different procedures. In this fashion, a normal program or short programs may be carried out or special programs may be provided such as e.g. treatment of biopsy samples. The controller is advantageously designed to provide different treatment programs. This is realized via an input means, data carriers or via a data line which is connected to a computer.

In an advantageous further development, the first treatment chamber is designed to receive several containers for several cartridges containing samples and the further treatment chamber is designed to receive such a container. This facilitates handling, since the containers for several cartridges may have the same design and are therefore suitable for supplying both treatment chambers. The further treatment chamber is designed to receive only one container to permit smaller sample charges to be subjected to abbreviated treatment or to complete examination of these samples on the same day, in view of a particular urgency. Of course, the second treatment chamber should also be able to receive other containers such as e.g. those designed to receive biopsy samples.

In one embodiment variant, the first treatment chamber is designed as a drum which can be rotated such that the containers can be immersed repeatedly into the respective treatment agent during rotation when the treatment chamber is partially filled with a treatment agent and a corresponding supply and removal of a respective treatment agent effects treatment in the further treatment chamber. This is, of course, only one example of different design and function of the treatment chambers. Numerous variations are thereby feasible which are associated with corresponding control programs.

A valve unit is preferably connected to the treatment chambers to supply the different treatment agents and to permit filling of each treatment chamber with the respective treatment agent, via the controller. Moreover, the valve unit and the controller may also be designed for emptying the treatment chamber and/or the lines.

The device may contain several treatment agent supply containers which are connected to the valve unit. Of course, the valve unit could also be connected to a central supply containing the most differing of treatment agents. In the former case, a further or the same valve unit and the controller are also advantageously designed to fill treatment agent into the supply container from a supply located outside of the device. This obviates the need for constant manual refilling and monitoring of the treatment agent supply containers and simplifies maintenance.

The invention is explained below with reference to the embodiments shown in the drawing.

DESCRIPTION OF THE PREFERRED EMBODIMENT

Figure 1:
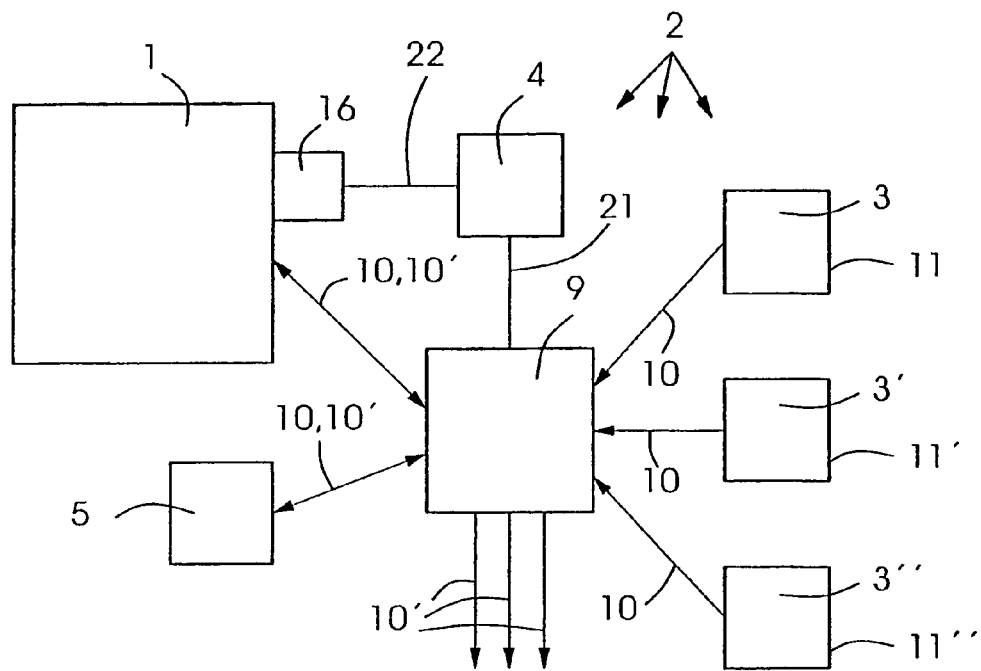
FIG. 1 shows a schematic diagram of the inventive device.

FIG. 1 shows a schematic diagram of the inventive device which schematically shows the individual elements. In addition to the treatment chamber 1, a further treatment chamber 5 is provided which is connected, via the same means 2, for supplying and removing treatment agents 3, 3' or 3". A valve unit 9 of appropriate design effects supply and removal of treatment agents 3, 3', 3" and is controlled by a controller 4 via a connection 21. The valve unit 9 obtains the treatment agents 3, 3', 3" via feed lines 10 which are connected e.g. to supply containers 11, 11', 11" having the treatment agents 3, 3', 3". These supply containers 11, 11', 11" may be located inside or outside of the device. Their number depends on the number of different treatment agents 3, 3', 3", . . . for the respective treatment. If the controller 4 is loaded with different treatment programs for the tissue samples, it is advantageous to provide as many treatment agents 3, 3', 3", . . . as are required for these programs. The controller 4 also comprises a connection 22 to the drive 16 of the drum 8 or 8' of the treatment chamber 1 to effect rotation of the drum 8 or 8' in correspondence with the treatment.

The valve unit 9 supplies the first treatment chamber 1 and the further treatment chambers 5 via feed lines 10 which may simultaneously serve as discharge lines 10'. It is possible to connect the same number of discharge lines 10' to the valve unit 9 as there are treatment agents 3, 3', 3" for processing. This permits separate discharge of the treatment agents 3, 3', 3" to be recycled. In the present case, only one further treatment chamber 5 is shown, as an example. Of course, further treatment chambers may be provided.

Figure 2:
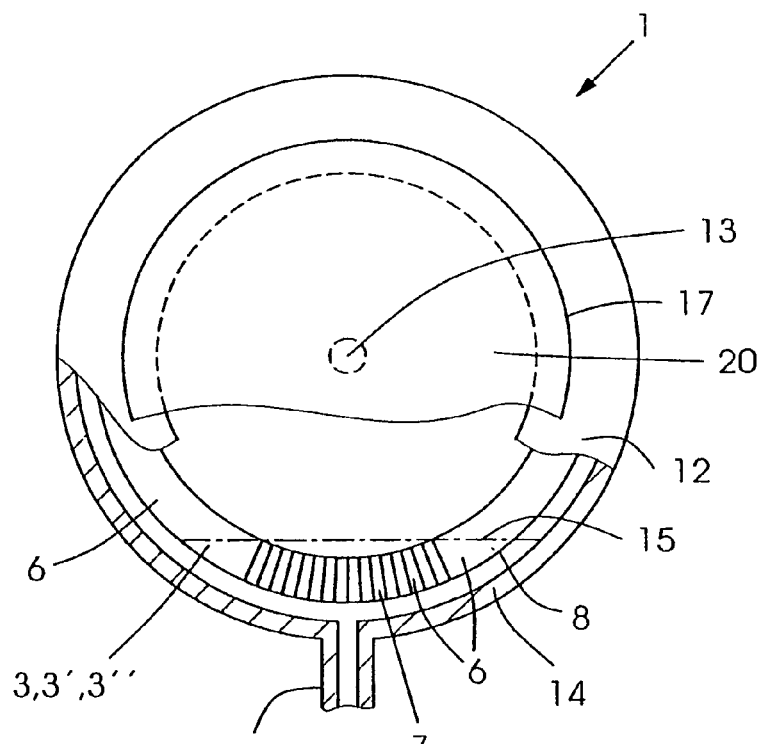
FIG. 2 shows the first treatment chamber of a first embodiment.

FIG. 2 shows the first treatment chamber 1 of a first embodiment of the invention. This treatment chamber 1 is formed by a cylindrical housing 14 in which a drum 8' is rotatably disposed. The likewise cylindrical drum 8' can be driven via an axle 13 and a drive 16 (not shown). The housing 14 has an inlet opening 20 at its front side which can be closed by a lid 17. The drum 8 surface bears containers 6 which each contain several cartridges 7 for samples. They are shown, by way of example, in the lower container 6. The front side of the housing 14 has an edge 12 with dimensions which assure that the liquid level 15 of a treatment agent 3, 3', 3" is sufficiently high, that all cartridges 7 with tissue samples are wet during rotation of the drum 8. This first treatment chamber 1 has a line 10, 10' for supply and removal of treatment agents 3, 3', 3", which is included in the inventive device (schematically shown in FIG. 1).

Figure 2A:
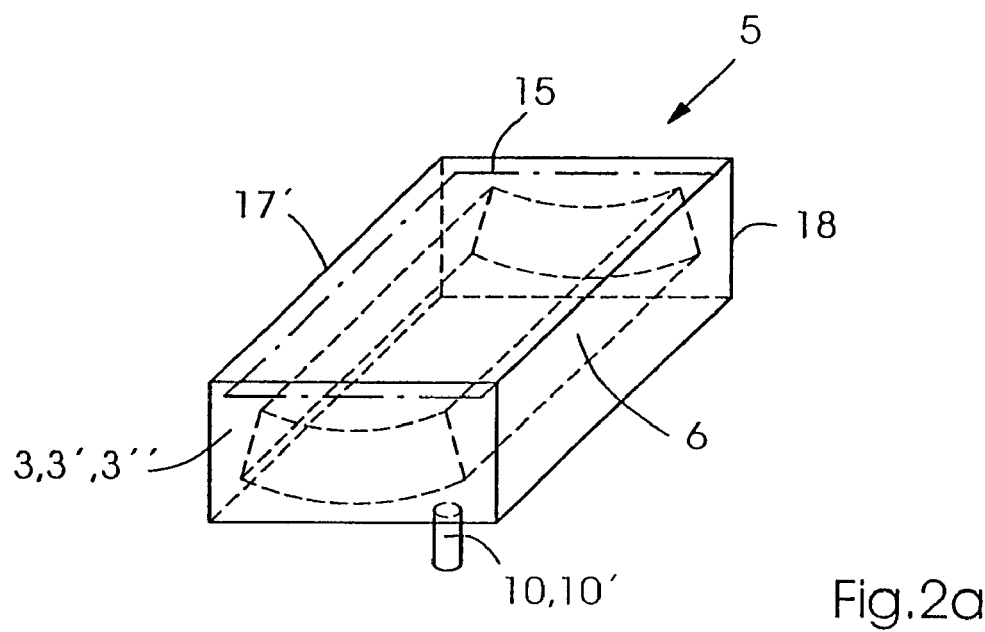
FIG. 2a shows the further treatment chamber of the first embodiment.

FIG. 2a shows the further treatment chamber 5 of this first embodiment. This treatment chamber 5 has a housing 18 with dimensions which permit reception of one of the containers 6 for cartridges 7 in that treatment chamber 5. The container 6 can be inserted into the treatment chamber 1 of FIG. 2. The housing 18 can be closed by a lid 17' and also comprises a line 10, 10' for supply and removal of treatment agents 3, 3', 3". Its size is such that the liquid level 15 of the treatment agent 3, 3', 3" can rise sufficiently high, that the container 6 is completely immersed in the treatment agent 3, 3', 3".

Figure 3:
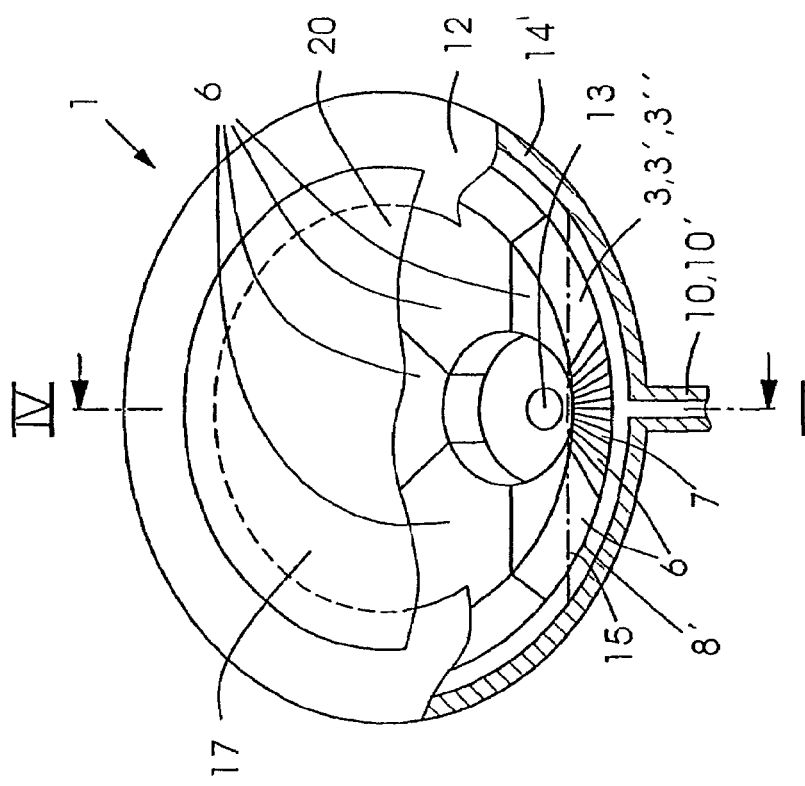
FIG. 3 shows the first treatment chamber of a second embodiment.

FIG. 3 shows the first treatment chamber 1 of a second embodiment. This first treatment chamber 1 has a truncated housing 14' which is disposed such that the peripheral surface intersects a horizontal line. This horizontal position and a corresponding edge 12 assure a liquid level 15 of a treatment agent 3, 3',3" which permits wetting of all cartridges 7 for samples (described already in connection with FIG. 2). Towards this end, the drum 8' also has a conical shape in correspondence with the housing 14' and has a narrow end comprising an axle 13, which is connected to a drive 16.

The housing 14' shown in FIG. 3 is cut in the lower region of the front side. This cut corresponds to III-III of FIG. 4. The edge 12 which holds the treatment agent 3, 3', 3" at liquid level 15 has thereby been omitted in this lower region of FIG. 3. The lid 17 which closes the access opening 20 is also cut open. The treatment chamber 1 has a conduit 10, 10' for supply and removal of treatment agent 3, 3', 3". This treatment chamber 1 of the second embodiment is also combined with the other elements shown therein in accordance with the schematic drawing of FIG. 1.

Figure 4A:
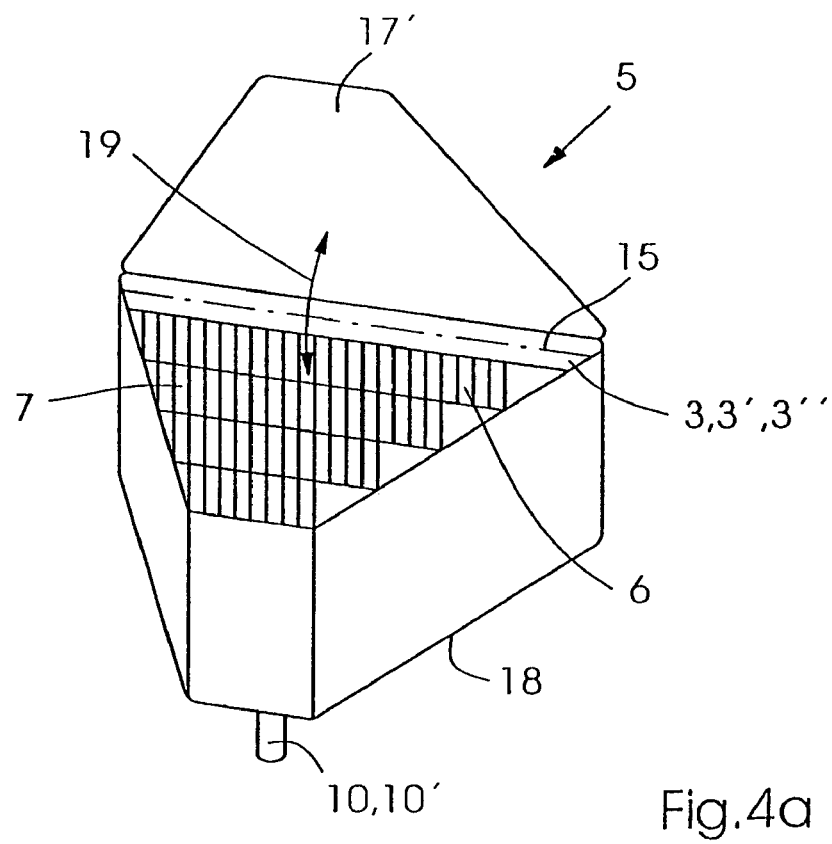
FIG. 4a shows the further treatment chamber of the second embodiment.
Figure 4:
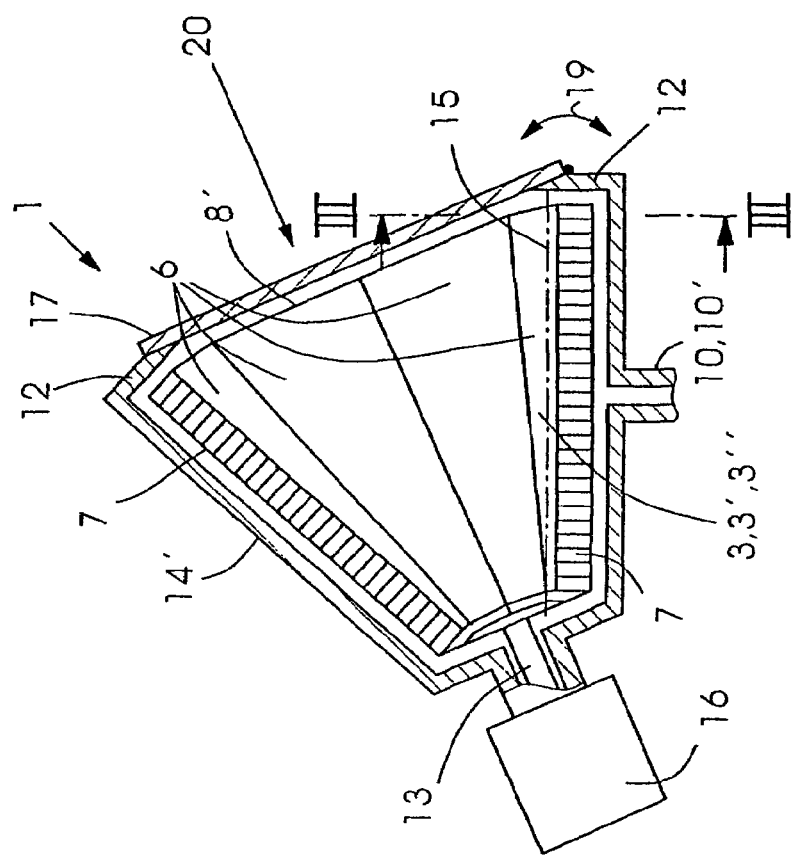
FIG. 4 shows a longitudinal section through this treatment chamber.

FIG. 4 shows a section IV-IV of FIG. 3 and explains the design of the treatment chamber 1 of the second embodiment in more detail. The lowermost layer of cartridges 7 for samples is thereby disposed completely below the liquid level 15 which is maintained by the edge 12 even when the lid 17 is opened (double arrow 19). This embodiment is particularly advantageous, since it provides good access to the containers 6 for the cartridges 7 even when the treatment agent 3, 3', 3" is located in the treatment chamber 1.

FIG. 4a shows the further treatment chamber 5 of the second embodiment. This further treatment chamber 5 is also designed to receive one of the containers 6 for cartridges 7 as already shown in FIGS. 3 and 4. Towards this end, the housing 18 and lid 17' have a trapezoidal shape to receive the containers 6. This trapezoidal shape facilitates their arrangement in the truncated conical drum 8'. Moreover, this further treatment chamber 5 functions in correspondence with that shown in FIG. 2a.

The designs of FIGS. 2 through 4a are of course only embodiments of the inventive device. The first treatment chambers 1 may have a similar design as shown for the further treatment chambers 5 or vice versa. The arrangement need not be confined to two treatment chambers 1 and 5 per device.

The user requirements are essential to the design of the individual treatment chambers 1, 5. The treatment chambers 1, 5 may have different designs with regard to size, configuration or type of wetting of the cartridges 7 with treatment agent 3, 3', 3". All conventional designs are thereby also possible. The core of the invention resides in the fact that several treatment chambers 1, 5 . . . can be supplied from a common valve unit 9 via a controller 4 and a means 2 for supplying and removing treatment agent 3, 3', 3" and that several treatments, which are adjusted to the respective requirements of the user, may be carried out simultaneously or in a time-staggered manner. In this fashion, the inventive device can replace two or more conventional devices while thereby requiring only one controller 4 and one means 2 for supplying and removing treatment agent 3, 3', 3". The supply containers 11, 11', 11" need not be disposed, maintained and filled separately for each treatment chamber 1, 5, etc.

UNITS FOR THE TREATMENT OF
HISTOLOGICAL SAMPLES

List of Reference Numerals

1 Treatment chamber (first)
2 Means for supply and removal of treatment agents
3,3',3" Treatment agents
4 Controller
5 Further treatment chambers
6 Containers for cartridges
7 Cartridges for samples
8,8' Drum
8 of the first embodiment
8' of the second embodiment
9 Valve unit
10,10' Lines
10 Feed line
10' Discharge line
11,11',11" Supply container
12 Edge
13 Axle
14,14' Housing of the first treatment chamber
14 of the first embodiment
14' of the second embodiment
15 Liquid level
16 Drive
17,17' Lid
17 of the first treatment chamber
17' of the second treatment chamber
18 Housing of the second treatment chamber
19 Double arrow: opening and closing of the lid
20 Access opening
21 Connection controller—valve unit
22 Connection controller—drive

I claim:

1. A device for preparing histological samples for processing in a microtome, the samples being disposed in cartridges which, in turn, are disposed in containers, the device comprising:

a first treatment chamber, said first treatment chamber having a drum for accepting the containers, said drum partially filled with a treatment agent;

means for rotating said drum such that the containers repeatedly dip into the treatment agent;

at least one second treatment chamber;

means for supplying and removing differing treatment agents to and from said first treatment chamber and said second treatment chamber; and a controller communicating with said supplying and removing means to control times of treatment agent supply and removal to and from said first treatment chamber and to and from said second treatment chamber, wherein treatments in said first and second chambers are carried out independently of each other.

2. The device of claim 1, wherein said first and said second treatment chambers are designed for different treatments.

3. The device of claim 2, wherein said first and said second treatment chambers have different designs.

4. The device of claim 3, wherein said second treatment chamber is structured and dimensioned to receive biopsy samples.

5. The device of claim 1, wherein said first and said second treatment chambers have different sizes.

6. The device of claim 5, wherein said second treatment chamber is substantially smaller than said first treatment chamber.

7. The device of claim 1, wherein said controller is designed to carry out different treatments.

8. The device of claim 7, wherein said controller is designed to carry out abbreviated programs.

9. The device of claim 7, wherein biopsy sample treatments can be carried out.

10. The device of claim 7, wherein said controller is designed to be supplied with different treatment programs.

11. The device of claim 1, wherein first treatment chamber is designed to receive several of the containers for several of the cartridges having samples and said second treatment chamber is designed to receive one of the containers.

12. The device of claim 1, wherein said supplying and removing means comprise a valve unit, wherein said controller causes said valve unit to be connected to said first and said second treatment chambers to fill said first and said second treatment chambers with a treatment agent required for a respective treatment.

13. The device of claim 12, wherein said valve unit and said controller are designed to also effect emptying of said first and said second treatment chambers.

14. The device of claim 13, wherein said valve unit is designed to vent feed lines.

15. The device of claim 12, further comprising a plurality of supply containers for treatment agent, said valve unit being connected to said supply containers.

16. The device of claim 15, wherein said valve unit and said controller are designed to fill said supply containers with treatment agents from a supply located outside of the device.

* * * * *